US011877762B2

(12) United States Patent
Fulkerson et al.

(10) Patent No.: US 11,877,762 B2
(45) Date of Patent: Jan. 23, 2024

(54) RETRIEVAL DEVICES HAVING PROTRUDING FEATURES FOR THROMBECTOMY

(71) Applicant: ReFlow Medical, Inc., San Clemente, CA (US)

(72) Inventors: John Fulkerson, Rancho Santa Margarita, CA (US); Isa Rizk, San Diego, CA (US); Jihad Ali Mustapha, Ada, MI (US); Teodoro S. Jimenez, Jr., Aliso Viejo, CA (US); Patrick Lo, Diamond Bar, CA (US)

(73) Assignee: REFLOW MEDICAL, INC., San Clemente, CA (US)

( * ) Notice: Subject to any disclaimer, the term of this patent is extended or adjusted under 35 U.S.C. 154(b) by 403 days.

(21) Appl. No.: 17/085,739

(22) Filed: Oct. 30, 2020

(65) Prior Publication Data
US 2021/0128184 A1    May 6, 2021

Related U.S. Application Data

(60) Provisional application No. 62/929,708, filed on Nov. 1, 2019.

(51) Int. Cl.
*A61B 17/221* (2006.01)

(52) U.S. Cl.
CPC .... *A61B 17/221* (2013.01); *A61B 2017/2215* (2013.01)

(58) Field of Classification Search
CPC ............ A61B 17/22031; A61B 17/221; A61B 2017/0427; A61B 2017/0435; A61B 2017/0437; A61B 2017/22034; A61B 2017/22035; A61B 2017/2212; A61B 2017/2215; A61B 2017/2217; A61F 2/01; A61F 2/0103; A61F 2/0105; A61F 2/0108; A61F 2/011; A61F 2/012; A61F 2/013; A61F 2/014; A61F 2/848;
(Continued)

(56) References Cited

U.S. PATENT DOCUMENTS

2003/0212430 A1* 11/2003 Bose ..................... A61B 17/221
606/200
2008/0125743 A1* 5/2008 Yuzhakov ......... A61M 37/0015
604/506
(Continued)

FOREIGN PATENT DOCUMENTS

CN      103417261      3/2016
CN      111388056      7/2020
(Continued)

OTHER PUBLICATIONS

International Search Report and Written Opinion from PCT/US2020/058364, dated Feb. 17, 2021, 35 pages.

*Primary Examiner* — Kankindi Rwego
(74) *Attorney, Agent, or Firm* — BAKERHOSTETLER

(57) ABSTRACT

A retrieval device can include inwardly facing protruding features that facilitate engagement and capture of a thrombus or other mass from a body lumen of a patient. The protruding features can deploy from a frame of the retrieval device to extend radially inwardly toward an opposing side of the frame. When deployed into a thrombus, the protruding features engage and urge the thrombus as the retrieval device moves to facilitate capture.

19 Claims, 9 Drawing Sheets

(58) Field of Classification Search
CPC .......... A61F 2002/015; A61F 2002/016; A61F 2002/018; A61F 2002/8483; A61F 2002/8486
USPC ........................................................ 606/200
See application file for complete search history.

(56) References Cited

U.S. PATENT DOCUMENTS

| | | | | |
|---|---|---|---|---|
| 2008/0269774 | A1* | 10/2008 | Garcia | A61B 17/221 |
| | | | | 606/127 |
| 2009/0306678 | A1* | 12/2009 | Hardert | A61B 17/221 |
| | | | | 606/127 |
| 2011/0054503 | A1 | 3/2011 | Rizk et al. | |
| 2013/0035750 | A1 | 2/2013 | Rizk et al. | |
| 2015/0209063 | A1 | 7/2015 | Rizk et al. | |
| 2016/0206334 | A1 | 7/2016 | Rizk et al. | |
| 2017/0100266 | A1 | 4/2017 | Fulkerson et al. | |
| 2017/0196717 | A1 | 7/2017 | Fulkerson et al. | |
| 2017/0258482 | A1* | 9/2017 | Davidson | A61N 1/378 |
| 2018/0289517 | A1 | 10/2018 | Jimenez et al. | |
| 2019/0201219 | A1 | 7/2019 | Fulkerson et al. | |
| 2020/0107947 | A1 | 4/2020 | Jimenez, Jr. et al. | |
| 2020/0129197 | A1* | 4/2020 | Follmer | A61B 17/221 |
| 2020/0214825 | A1* | 7/2020 | Gassler | A61F 2/07 |
| 2021/0378692 | A1* | 12/2021 | Xiang | A61B 17/221 |

FOREIGN PATENT DOCUMENTS

| | | |
|---|---|---|
| WO | WO 2010/034021 | 3/2010 |
| WO | WO 2019/055311 | 3/2019 |

\* cited by examiner

RETRIEVAL DEVICES HAVING PROTRUDING FEATURES FOR THROMBECTOMY

CROSS-REFERENCE TO RELATED APPLICATION

This application claims the benefit of U.S. Provisional Application No. 62/929,708, entitled "STENTS HAVING PROTRUDING FEATURES FOR THROMBECTOMY," filed Nov. 1, 2019, the entirety of which is incorporated herein by reference.

TECHNICAL FIELD

The present description relates generally to mechanical removal of objects from within a body. In particular, described herein are devices and methods for thrombectomy.

BACKGROUND

It is often desirable to remove tissue from the body in a minimally invasive manner as possible, so as not to damage other tissues. For example, removal of tissue from within a vasculature, such as blood clots, may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Formation of a blood clot in a vein deep in the body is known as deep vein thrombosis. Deep vein thromboses, such as those that occur in the lower leg or thigh, can form in a vein that may subsequently swell, and the deep vein thrombosis can break loose and cause a blockage lung, known as a pulmonary embolism.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Figure 1:
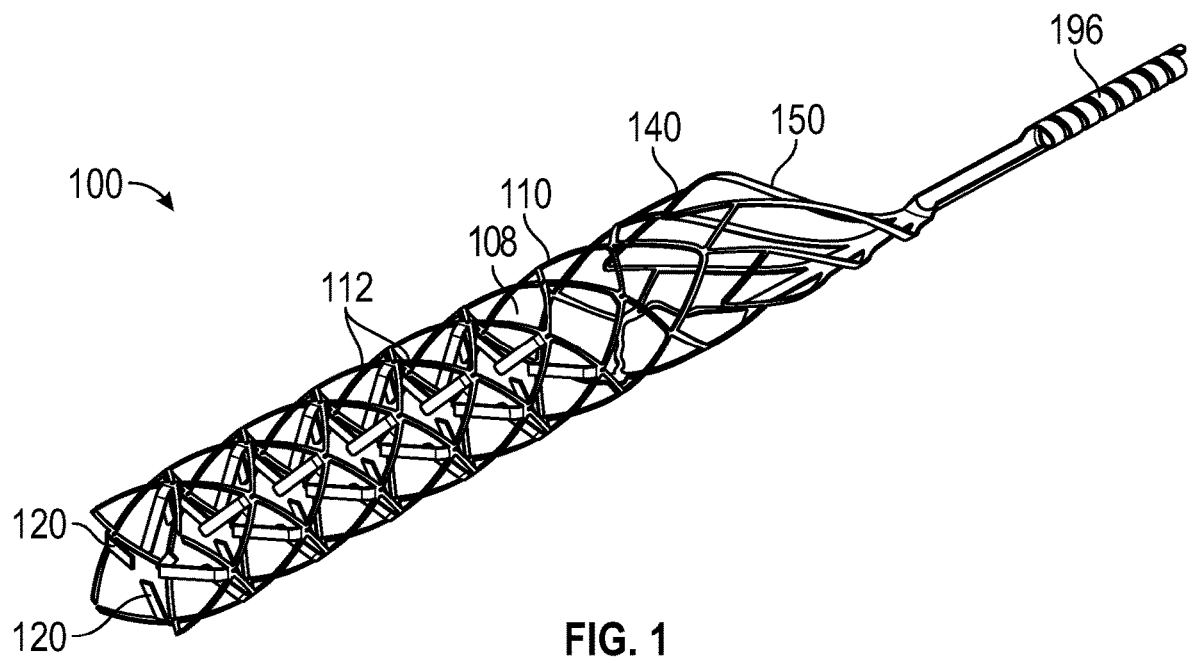
FIG. 1 shows a perspective view of an example of a retrieval device, according to some embodiments of the present disclosure.
Figure 2:
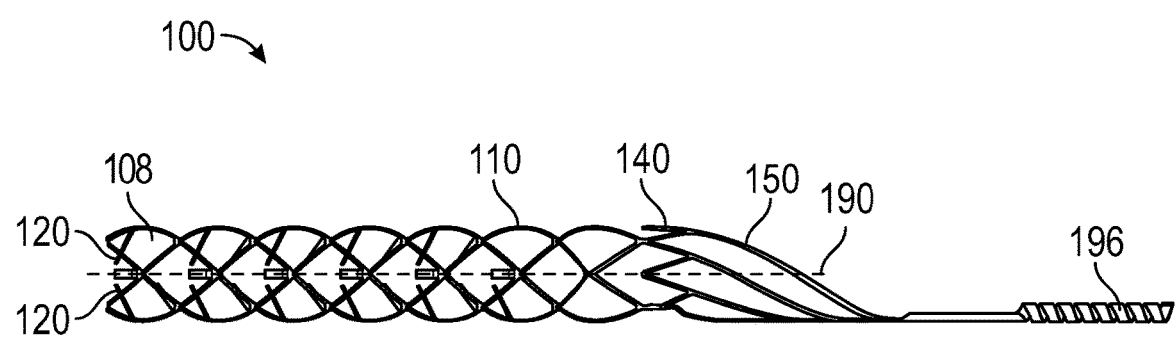
FIG. 2 shows a side view of the retrieval device of FIG. 1, according to some embodiments of the present disclosure.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

The following disclosure describes various embodiments of devices, systems, and methods for employing expandable structures, such as retrieval devices or scaffolds, having spikes, flails, or other inwardly or outwardly protruding features for removing, modifying, transporting, and/or mitigating a thrombus or other mass within a human patient, and associated devices and methods. The delivery systems can be configured to deliver and position expandable structures within a body lumen (e.g., vessel). In addition, these delivery systems can also be configured to deploy and expand the expandable structures in the body lumen. The expandable structures can be configured to engage a thrombus or other mass within a human patient. The delivery systems can further be configured to interact with the expanded structure and collapse the structure for removal from the body lumen, along with the thrombus or other mass.

Certain details are set forth in the following description and FIGS. 1-27 to provide a thorough understanding of various embodiments of the disclosure. To avoid unnecessarily obscuring the description of the various embodiments of the disclosure, other details describing well-known structures and systems often associated with expandable structures, inwardly or outwardly protruding features, and the components or devices associated with the manufacture of such structures are not set forth below. Moreover, many of the details and features shown in the figures are merely illustrative of particular embodiments of the disclosure. Accordingly, other embodiments can have other details and features without departing from the spirit and scope of the present disclosure. A person of ordinary skill in the relevant art will therefore understand that the present technology, which includes associated devices, systems, and procedures, may include other embodiments with additional elements or steps, and/or may include other embodiments without several of the features or steps shown and described below with reference to FIGS. 1-27. Furthermore, various embodiments of the disclosure can include structures other than those illustrated in the figures and are expressly not limited to the structures shown in the figures.

As shown in FIGS. 1-4, an expandable retrieval device 100 is provided with a frame 110 and multiple inwardly extending protruding features 120. The frame 110 can be configured to radially outwardly expand after the retrieval device 100 has been unsheathed from a delivery shaft. The protruding features 120 can be configured to radially inwardly expand from the frame 110 as the retrieval device 100 is unsheathed from the delivery shaft and/or as the frame 110 expands radially outwardly.

The retrieval device 100 can be self-expanding upon release from a constraint. Additionally or alternatively, the retrieval device 100 can be expandable by an external stimulus (e.g., mechanical force, thermal stimulus, chemical reaction, etc.). The frame 110 can include multiple struts 112 arranged in a pattern that supports compression, expansion, flexibility, and bendability of the retrieval device 100. The struts 112 can be connected to each other to form openings 108 that extend through the frame 110, such as from a lumen within the frame 110 to an exterior of the frame 110. The frame 110 can form a generally cylindrical shape along at least a portion of the retrieval device 100. At least a portion of each protruding feature 120 can extend at least partially inwardly from the frame 110 (e.g., towards the distal end of the retrieval device 100). For example, at least a portion of each protruding feature 120 can extend parallel to a longitudinal axis of the retrieval device 100. At least a portion (e.g., terminal end portion) of each protruding feature 120 can extend at least partially radially inwardly from the frame 110. By further example, at least a portion of each protruding feature 120 can extend distally and/or proximally from the frame 110.

Additionally or alternatively, at least some protruding features 120 can be configured to radially outwardly expand from the frame 110 as the retrieval device 100 is unsheathed from the delivery shaft and/or as the frame 110 expands radially outwardly. Such protruding features can facilitate interaction with the thrombus outside of the frame 110. For example, outwardly protruding features can scrape a thrombus or portions thereof off of a vessel wall as the retrieval device 100 is moved within a blood vessel.

The frame 110, struts 112, and/or protruding features 120 can be composed of or formed from a variety materials including, e.g., nitinol, cobalt chromium, stainless steel, any of a variety of other metals or metal alloys, or a combination thereof. The frame 110, struts 112, and/or protruding features 120 may also be composed of or formed from bioresorbable biodegradable, nanoporous or non-bioresorbable, non-biodegradable, non-nanopourous materials including, e.g., one or more polymers, nitinol, plastic materials, etc., or a combination thereof. In some embodiments, the frame 110 and the struts 112 can be formed from a bioresorbable material and the protruding features 120 can be formed from a non-bioresorbable material, such as nitinol.

The protruding features 120 may also be carried by more than one strut 112, the frame 110, or a combination thereof. The protruding features 120 may be integrally and/or monolithically formed with the frame (e.g., the struts 112), for example by bending or twisting a portion of one or more struts and/or the frame 110 toward a longitudinal axis of the retrieval device 100 or, alternatively, the protruding features 120 may be separate, discrete components that are attached to desired locations along the struts 112 and/or the frame 110.

Figure 3:
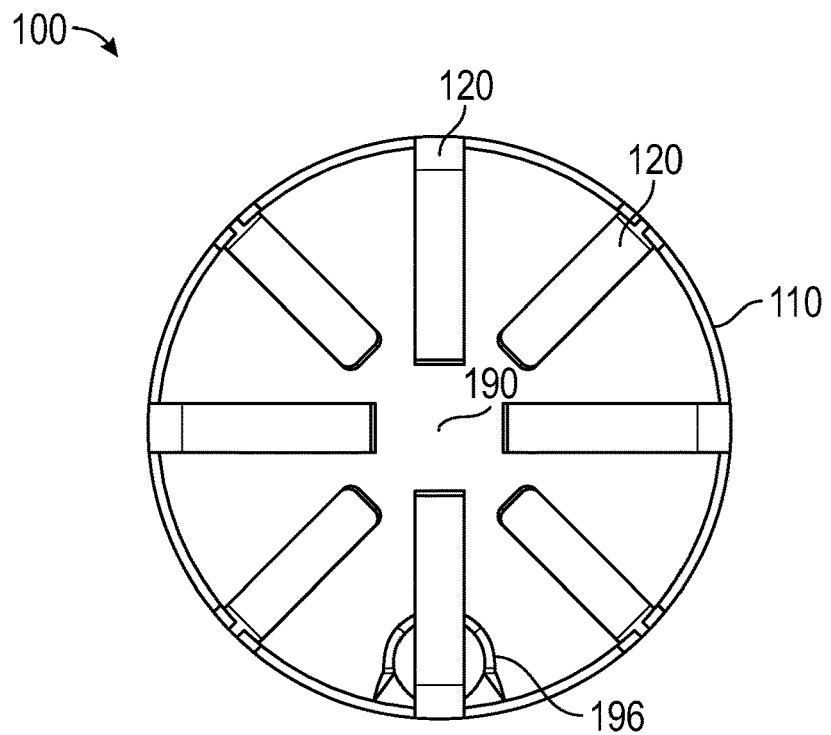
FIG. 3 shows a front view of the retrieval device of FIG. 1, according to some embodiments of the present disclosure.

The protruding features 120 can be contained within an outer periphery of the frame 110 while the retrieval device 100 is in a collapsed configuration and/or when the retrieval device 100 is in an expanded configuration. For example, the protruding features 120 can be positioned within the openings 108 between multiple struts 112. Each of the protruding features 120 can move to extend at least partially toward a central axis 190 of the retrieval device 100. For example, as shown in FIG. 3, each of the protruding features 120 can extend toward, but not reach, the central axis 190 and thereby not contact or cross each other. The protruding features 120 can include one or more of a variety of shapes and features. For example, the protruding features 120, or portions thereof, can be straight, curved, helical, and/or spiral. The protruding features 120 can have the same or different sizes, shapes, and/or features relative to each other.

The protruding features 120 can have the same or different axial positions, circumferential positions, and/or orientations (e.g., proximal or distal facing). For example, at least some of the protruding features 120 can be axially aligned and arranged with different circumferential positions and/or orientations. By further example, at least some of the protruding features 120 can be circumferentially aligned and arranged with different axial positions and/or orientations. By further example, at least some of the protruding features 120 can have the same orientation and be arranged with different axial and/or circumferential positions. At least some of the protruding features 120 can have different axial and circumferential positions. At least some of the protruding features 120 can have different axial positions and orientations. At least some of the protruding features 120 can have different circumferential positions and orientations.

Figure 4:
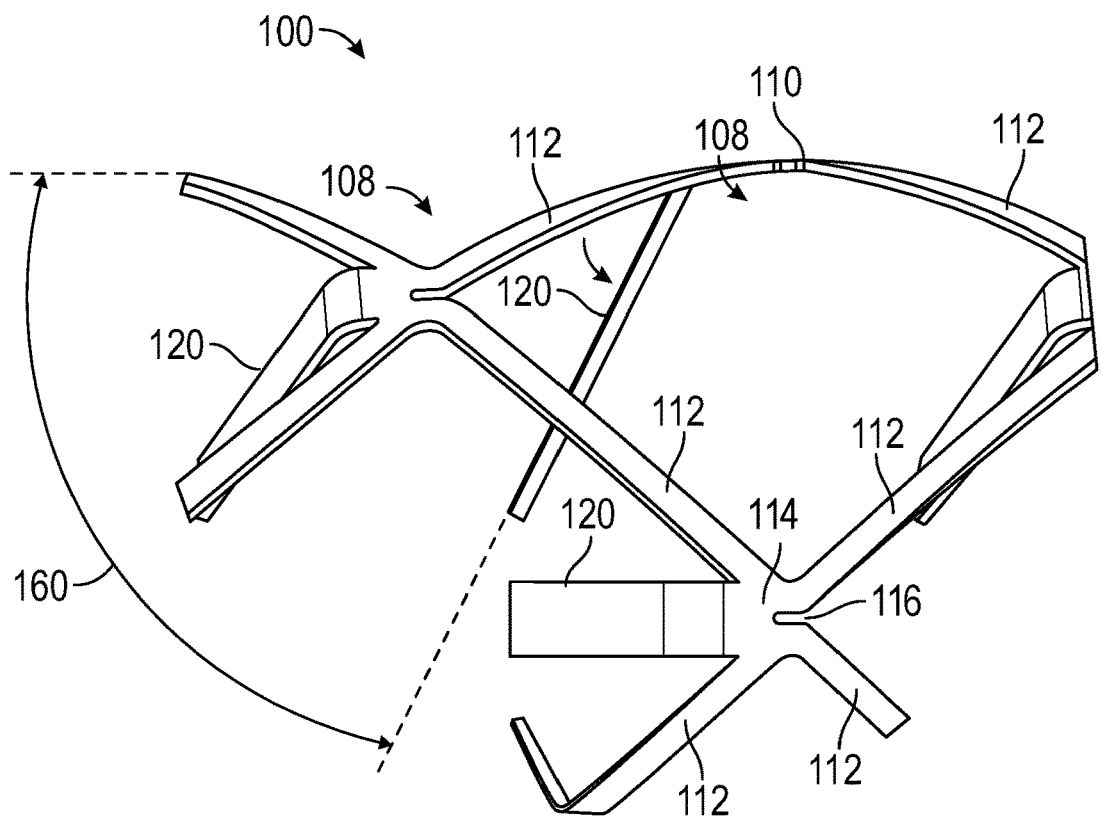
FIG. 4 shows an enlarged view of a portion of the retrieval device of FIG. 1, according to some embodiments of the present disclosure.

As shown in FIG. 4, the struts 112 can be connected to each other and arranged, such that multiple struts 112 (e.g., 2, 3, 4, 5, 6, 7, 8, or more than 8 struts) are connected together at a vertex 114. The protruding features 120 can each extend from a corresponding vertex 114. For example, the protruding features 120 can extend from a vertex 114 at an end of an opening 108. As such, the protruding features 120 can have only one end connected to the frame 110.

The frame 110 can form gaps 116 at the vertices 114 to facilitate collapse and expansion of the frame 110. For example, the struts 112 can be allowed to move toward and away from each other to facilitate transition of the frame 110. Such movement can be enhanced by providing gaps 116, as shown in FIG. 4. The gaps 116, for example, can be positioned on a side of the vertex 114 that is opposite the corresponding protruding feature 120 that extends from the vertex 114. In some examples, the gaps 116 can extend longitudinally with parallel edges, although other shapes are contemplated. Accordingly, the frame 110 can provide ample flexibility for transitioning between the collapsed and expanded configurations.

The protruding features 120 can move (e.g. from the collapsed configuration to the expanded configuration) to form an angle 160 as they extend radially inwardly from the frame 110. In the collapsed configuration, the protruding features 120 can extend generally longitudinally or more longitudinally. In the expanded configuration, the protruding features 120 can extend at least partially radially inwardly. The angle 160 formed thereby (e.g., with respect to the frame 110 and/or a reference that is parallel to the central axis of the frame 110) can be any angle (e.g., from 0 to 90 degrees). The angle 160 can be selected during formation so that the angle 160 is formed when the retrieval device 100 expands when deployed. The angle 160 can be formed on a distally facing side or a proximally facing side of the corresponding protruding feature 120. The angle 160 can be equal to, less than, and/or greater than 0, 10, 20, 30, 40, 50, 60, 70, 80, or 90 degrees. The angle 160 can be the same or different for any two protruding features 120.

Referring now to FIGS. 5-9, the protruding features 120 can have one or more of a variety of features and/or shapes to facilitate engagement with a thrombus or other mass.

Figure 5:
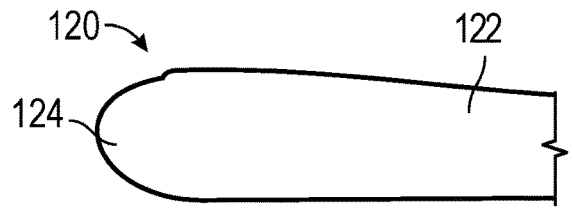
FIG. 5 shows a view of an example of a protruding feature, according to some embodiments of the present disclosure.

As shown in FIG. 5, one or more of the protruding features 120 can include a stem 122 and a head 124 with a rounded shape. The rounded head 124 can be sized to facilitate engagement with a thrombus or other mass while remaining atraumatic with respect to other structures.

Figure 6:
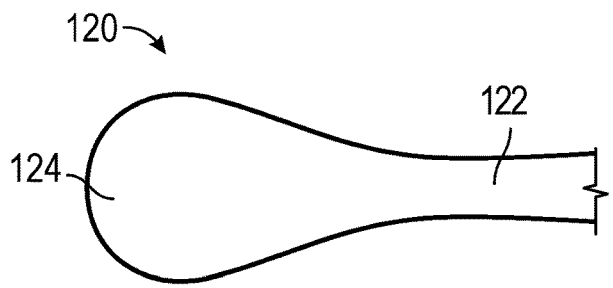
FIG. 6 shows a view of another example of a protruding feature, according to some embodiments of the present disclosure.

As shown in FIG. 6, one or more of the protruding features 120 can include a stem 122 and an enlarged head 124 at a terminal end of the protruding feature 120. For example, the head 124 can have a width or other dimension that is greater than that of the stem 122. The enlarged head 124 can be sized to cover a broad area to increase the engagement with a thrombus or other mass.

Figure 7:
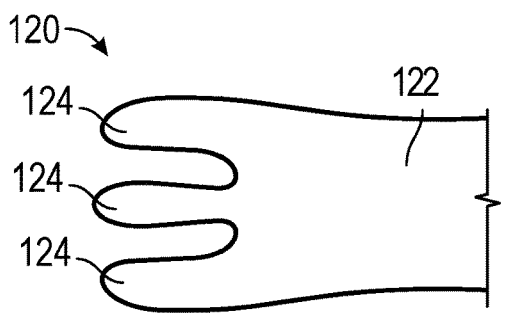
FIG. 7 shows a view of another example of a protruding feature, according to some embodiments of the present disclosure.

As shown in FIG. 7, one or more of the protruding features 120 can include a stem 122 and multiple heads 124 that are spaced apart from each other at a terminal end of the protruding feature 120. The multiple heads 124 can be sized and distributed to cover a broad area while maintaining flexibility.

Figure 8:
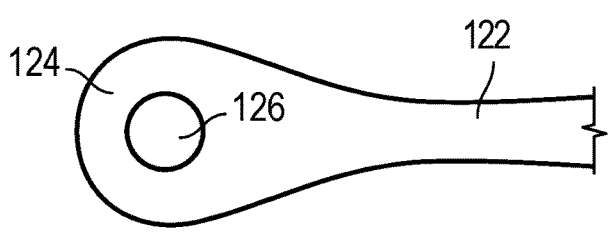
FIG. 8 shows a view of another example of a protruding feature, according to some embodiments of the present disclosure.

As shown in FIG. 8, one or more of the protruding features 120 can include a stem 122 and a head 124 with a loop that provides an opening 126 extending through the head 124 of the protruding feature 120. The loop can cover a broad area while allowing passage there through.

Figure 9:
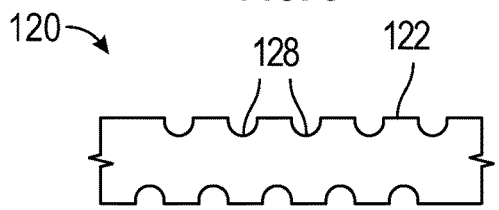
FIG. 9 shows a view of another example of a protruding feature, according to some embodiments of the present disclosure.

As shown in FIG. 9, one or more of the protruding features 120 can include surface features 128 along an exterior surface thereof at the stem 122 and/or the head. The surface features 128 can include notches, cuts, divots, dimples, ridges, channels and the like forming patterned textures. The surface features 128 can be distributed along the length of the protruding feature 120. Any given protruding feature 120 can include one or more of a variety of different surface features.

Referring again to FIGS. 1 and 2, the retrieval device 100 can include an enlarged section 140 proximal to the frame 110. The enlarged section 140 can be integrally and/or monolithically formed with the frame 110. The enlarged section 140 can provide, in an expanded configuration, an outer dimension that is greater than an outer dimension of the frame 110. Accordingly, the enlarged section 140 can engage and/or scrape against a vessel wall of a body lumen to separate a thrombus or other mass from the vessel wall when the retrieval device 100 is moved along the vessel wall. The enlarged section 140 can have protrusions or other heads 124 that are directed distally along the retrieval device 100.

The retrieval device 100 can include an anchor portion 196 that securely connects to a component for controlling, positioning, and/or adjusting the retrieval device 100. For example, the anchor portion 196 can securely connect the retrieval device 100 to a positioner or other member. The anchor portion 196 can be offset from a central axis 190 of the retrieval device 100. For example, the anchor portion 196 can be radially aligned with, adjacent to, or near a portion of the frame 110 of the retrieval device 100. The frame 110 of the retrieval device 100 can be connected to the anchor portion 196 by an intermediate portion 150. The intermediate portion 150 can include multiple struts that may have varying widths to aide in column strength for deploying and retraction that extend from different portions of the frame 110, for example connecting to different circumferential portions at an end of the frame 110. The struts of the intermediate portion 150 can extend to the same or different axial locations along the anchor portion 196. The arrangement of the struts of the intermediate portion 150 can maintain an open central space along the entire length of the retrieval device 100. The intermediate portion 150 can engage and/or scrape against a vessel wall of a body lumen to separate a thrombus or other mass from the vessel wall when the retrieval device 100 is moved along the vessel wall.

Figure 10:
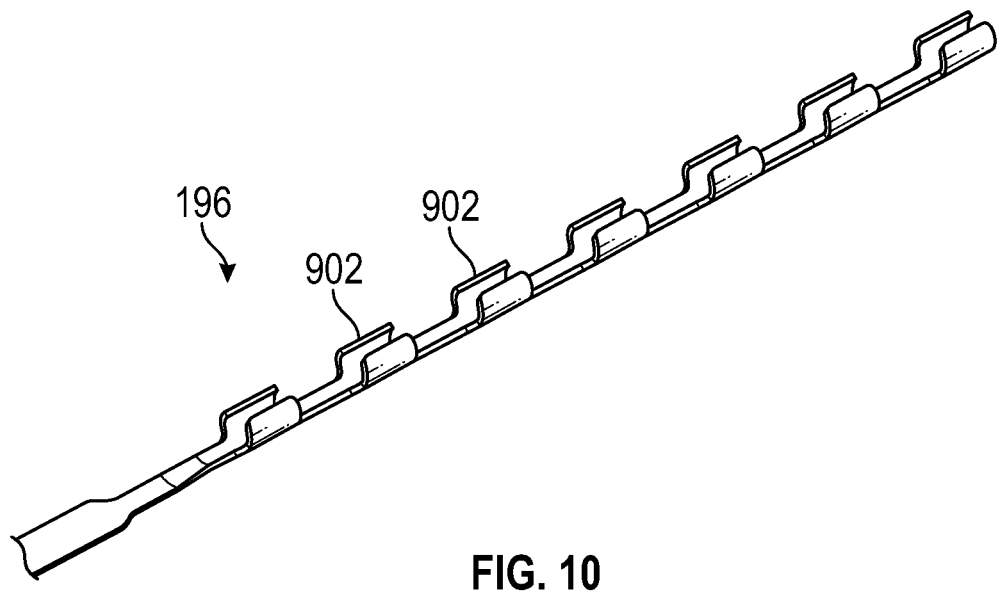
FIG. 10 shows a perspective view of an example of a connector end of the retrieval device of FIG. 1, according to some embodiments of the present disclosure.

As shown in FIGS. 10-13, the anchor portion 196 can be formed with one or more of a variety of arrangements. As shown in FIG. 10, the anchor portion 196 can include multiple ribs 902 extending circumferentially from different axial locations along the anchor portion 196. The ribs 902 can be positioned at different axial locations to provide multiple points of contact with a positioner.

Figure 11:
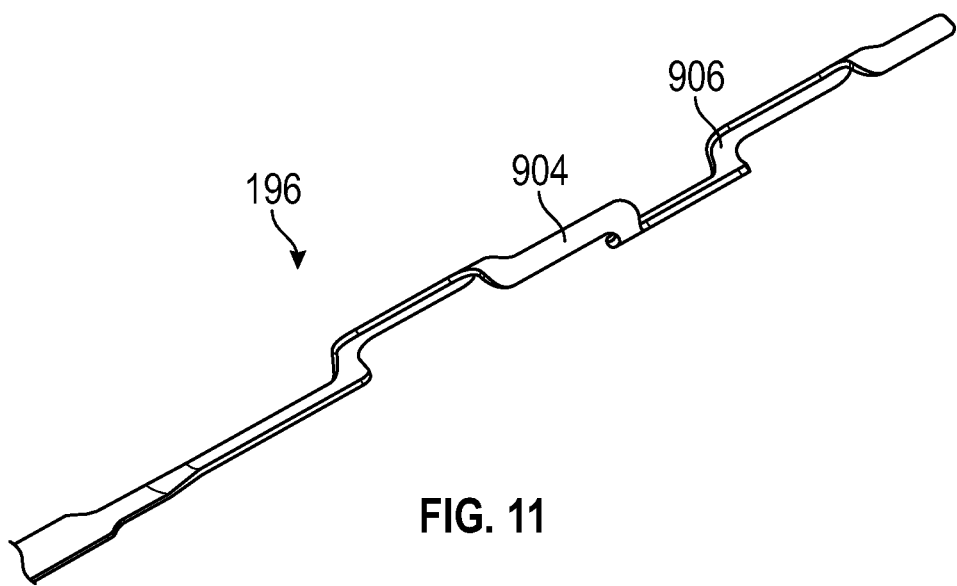
FIG. 11 shows a perspective view of another example of a connector end of the retrieval device of FIG. 1, according to some embodiments of the present disclosure.

As shown in FIG. 11, the anchor portion 196 can include different portions that extend in different directions. For example, the anchor portion 196 can include longitudinal portions 904 and circumferential portions 906. Axially adjacent pairs of the longitudinal portions 904 can be connected together by a corresponding circumferential portion 906. Likewise, axially adjacent pairs of the circumferential portions 906 can be connected together by a corresponding longitudinal portion 904. Different longitudinal portions 904 can have different circumferential positions to surround a coupled positioned at different circumferential positions thereon.

Figure 12:
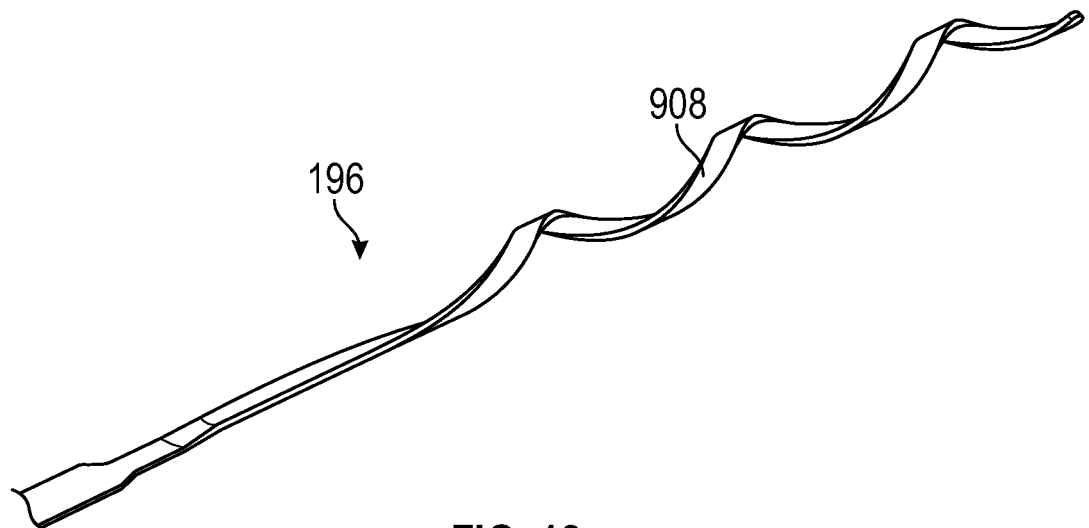
FIG. 12 shows a perspective view of another example of a connector end of the retrieval device of FIG. 1, according to some embodiments of the present disclosure.

As shown in FIG. 12, the anchor portion 196 can include a helical winding 908. For example, the anchor portion 196 can wind helically about a central space configured to receive the positioner therein. The helical winding 908 can include multiple (e.g., 2, 3, 4, 5, 6, 7, 8, or more than 8) turns. The helical winding 908 can include, in cross-section, a shape that provides a flat inner side for engaging the positioner while maintaining a low profile.

Figure 13:
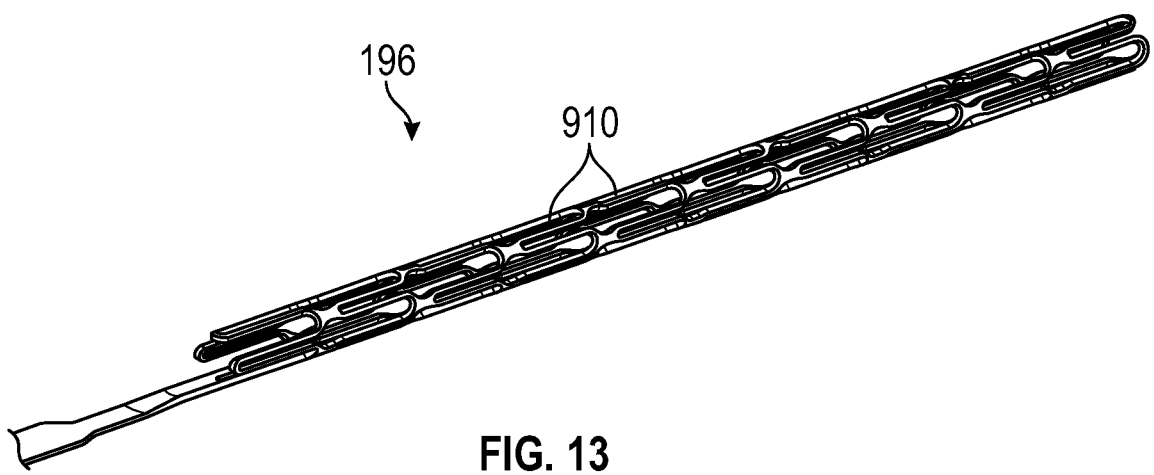
FIG. 13 shows a perspective view of another example of a connector end of the retrieval device of FIG. 1, according to some embodiments of the present disclosure.

As shown in FIG. 13, the anchor portion 196 can include an arrangement of multiple struts 910. The struts 910 can define a generally cylindrical shape for receiving and coupling to a positioner. The struts 910 can extend longitudinally and/or circumferentially about the space for receiving the positioner. The struts 910 can form any number of cells, which can vary in length and/or width relative to each other.

The anchor portion 196 can securely connect the retrieval device 100 to a positioner. For example, the anchor portion 196 can be pressed onto the positioner. By further example, the anchor portion 196 can be bonded to the positioner. Additionally or alternatively, a sleeve can be provided about at least a portion of the anchor portion 196 and/or the positioner. For example, a tube, such as shrink tubing molded from one or more flexible materials, including polyurethane and Pebex® (e.g., Pebex® 35D), can be provided as a sleeve over the anchor portion 196 and/or the positioner. Additionally or alternatively, the anchor portion 196 can removably or reversibly connect the retrieval device 100 to a positioner. For example, the anchor portion 196 can be provided with one or more detachment mechanisms (e.g., electrolytic, mechanical, or chemical) for controllably separating the retrieval device 100 from the positioner. As such, the retrieval device 100 can be controllably detached and left at a target delivery location.

Figure 14:
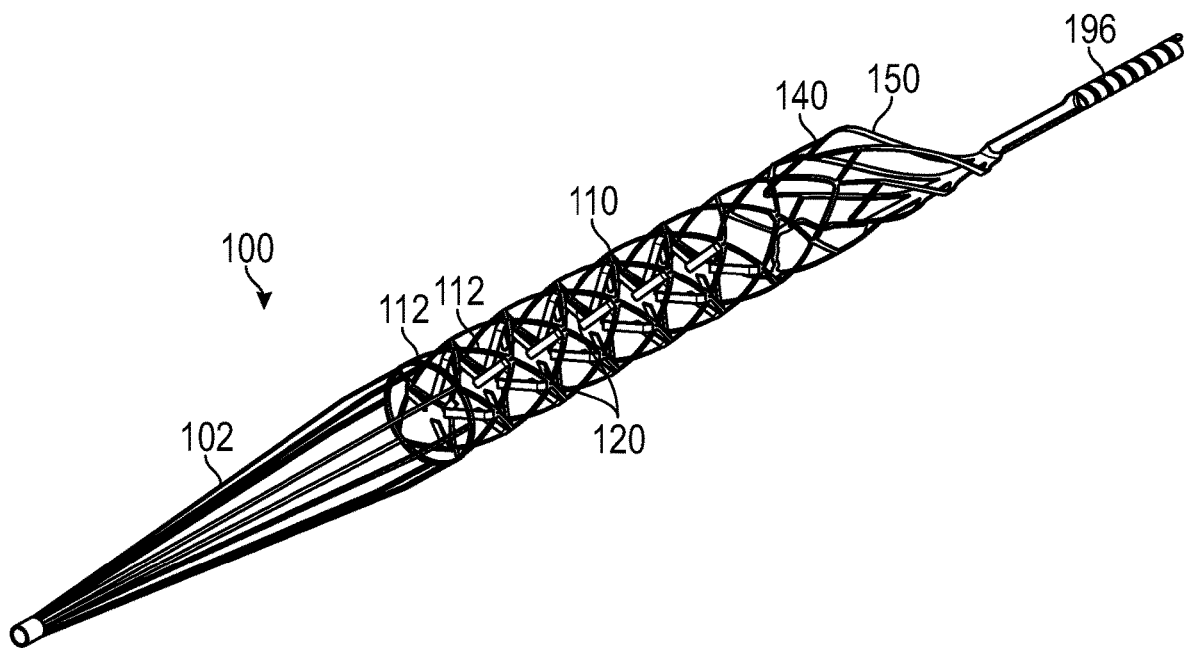
FIG. 14 shows a perspective view of another example of a retrieval device, according to some embodiments of the present disclosure.
Figure 15:
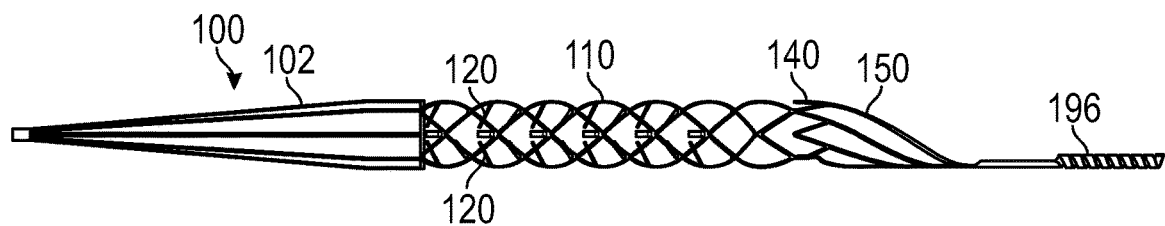
FIG. 15 shows a side view of the retrieval device of FIG. 14, according to some embodiments of the present disclosure.
Figure 16:
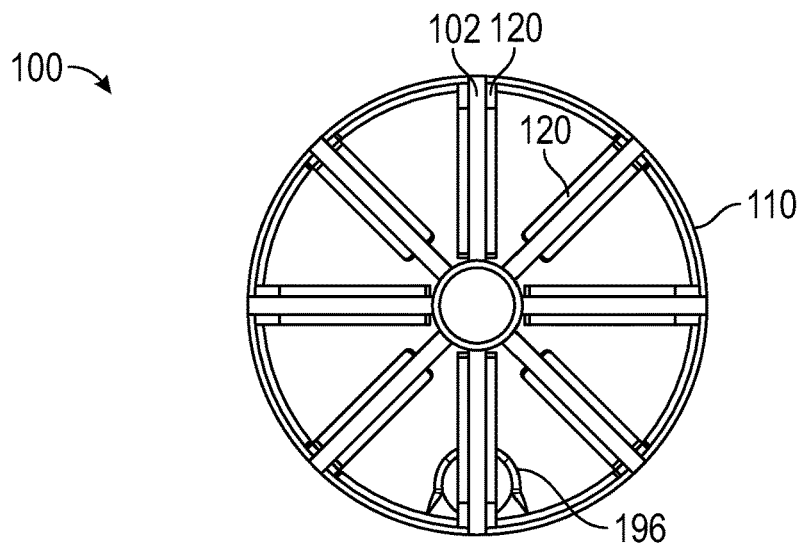
FIG. 16 shows a front view of the retrieval device of FIG. 14, according to some embodiments of the present disclosure.

FIGS. 14-16 illustrate a modified expandable retrieval device 100 having several features in common with the retrieval device 100 illustrated in FIGS. 1-13. Accordingly, common features are designated with the same numbering as used in FIGS. 1-13, and the description above will be understood to apply to the retrieval device 100 of FIGS. 14-16.

As shown in FIGS. 14-16, the retrieval device 100 can optionally include a capture member 102 at a distal end of the retrieval device 100. The capture member 102 can provide engagement and/or capturing features to interact with a thrombus or other mass as the retrieval device 100 is operated. For example, the capture member 102 can be used to engage a distal end of a thrombus or other mass while the frame 110 or other portion of the retrieval device 100 and engages other portions of the thrombus or other mass. By further example, the capture member 102 can be used to capture debris from a thrombus, other mass, and/or other debris from any location.

The capture member 102 can include struts or other features that extend distally from a distal end of the frame 110. The capture member 102 can taper from an outer diameter of the frame 110 to a smaller diameter at a distal end of the retrieval device 100. The struts or other features of the capture member 102 can be integrally and/or monolithically formed with the frame 110 and/or other portions of the retrieval device 100. Alternatively, the capture member 102 may form separate, discrete components that are attached to desired locations at the frame 110.

In some embodiments, the capture member 102 can include a material (e.g., PTFE, Dacron, polyamides, such as nylon and/or polyurethane based materials, silicone, etc.) positioned over, for example, struts of the capture member 102. In some embodiments, the material covers the entire outer surface area of the capture member 102. The material can be a mesh or a braid. In some embodiments, the material can further be configured to allow blood flow through the inner diameter of the retrieval device 100 and/or limit blood flow to an outer dimension of the retrieval device 100. In addition, the material can be configured to prevent debris from the wall of the body lumen (e.g. from a thrombus or other mass) from entering the bloodstream.

Figure 17:
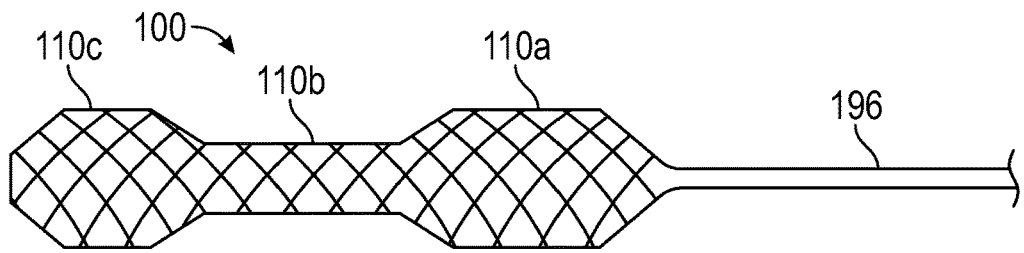
FIG. 17 shows a side view of another example of a retrieval device, according to some embodiments of the present disclosure.

FIG. 17 illustrates a modified expandable retrieval device 100 having several features in common with the retrieval devices 100 illustrated in FIGS. 1-16. Accordingly, common features are designated with the same numbering as used in FIGS. 1-16, and the description above will be understood to apply to the retrieval device 100 of FIG. 17.

As shown in FIG. 17, the retrieval device 100 can be expanded into a thrombus, clot, or other mass for interaction there with. Where a portion of the thrombus is aligned with the middle frame segment 110b, such a portion can be captured between opposing end frame segments, such as a proximal frame segment 110a and a distal frame segment 110c. The end frame segments 110a and 110c can have an outer cross-sectional dimension (e.g., diameter) that is greater than an outer cross-sectional dimension (e.g., diameter) of the middle frame segment 110b. As the retrieval device 100 is moved, the thrombus can be urged by the end frame segments 110a and 110c, as well as the middle frame segment 110b, as well as the transitions (e.g., tapered or stepped portions) there between and/or formed thereby. Accordingly, the frame, in addition to the protruding features, can engage the thrombus to facilitate movement thereof.

Figure 18:
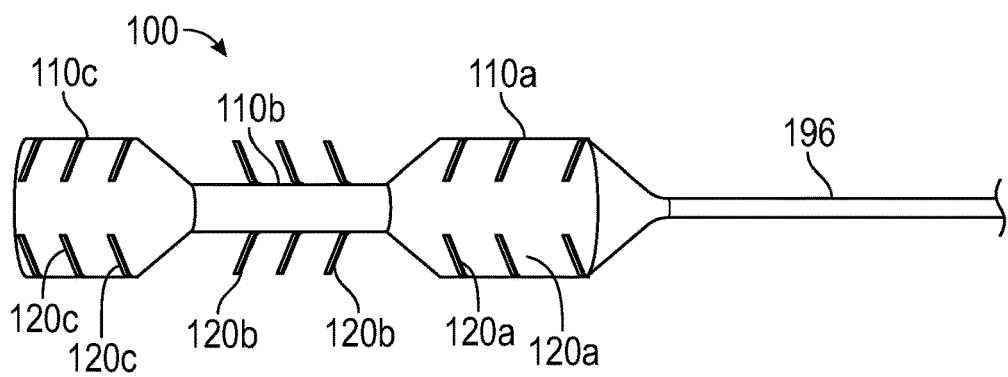
FIG. 18 shows a side view of another example of a retrieval device, according to some embodiments of the present disclosure.

FIG. 18 illustrates a modified expandable retrieval device 100 having several features in common with the retrieval devices 100 illustrated in FIGS. 1-17. Accordingly, common features are designated with the same numbering as used in FIGS. 1-17, and the description above will be understood to apply to the retrieval device 100 of FIG. 18.

As shown in FIG. 18, the retrieval device 100 can include a frame having one or more end frame segments and a middle frame segment between and/or adjacent to the one or more end frame segments. The end frame segments, such as a proximal frame segment 110a and a distal frame segment 110c and/or the middle frame segment 110b can have one or more of the features described herein with respect to the frame 110. The end frame segments 110a and 110c can have an outer cross-sectional dimension (e.g., diameter) that is greater than an outer cross-sectional dimension (e.g., diameter) of the middle frame segment 110b. The end frame segments 110a and 110c can have protruding features, such as proximal protruding features 120a and distal protruding features 120c, extending radially inwardly from the corresponding end frame segment 110a and 110c. The middle frame segment 110b can have protruding features 120b extending radially outwardly from the middle frame segment 110b. The protruding features 120a and/or 120b can have one or more of the features described herein with respect to the protruding features 120. Optionally, the middle protruding features extending from the middle frame segment 110b can, in the expanded configuration, radially extend no farther than the outer cross-sectional dimension (e.g., diameter) of the end frame segments 110a and/or 110c. As such, the end frame segments 110a and 110c can define the outermost radial extent of the frame 110. The protruding features 120a can facilitate engagement with a thrombus from within the end frame segments 110a and 110c, and the protruding features 120b can facilitate engagement with a thrombus from outside the middle frame segment 110b.

Figure 19:
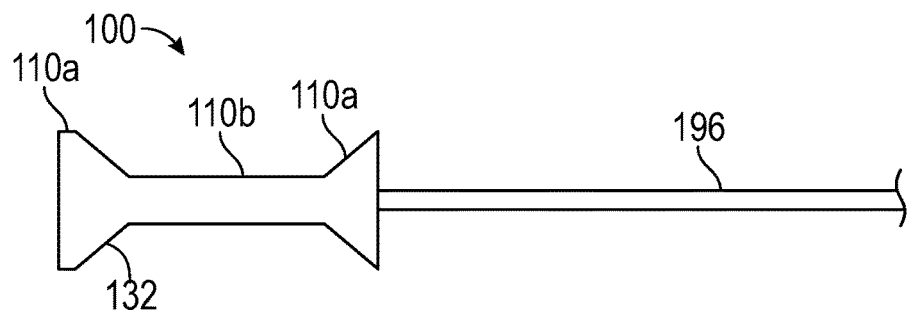
FIG. 19 shows a side view of another example of a retrieval device, according to some embodiments of the present disclosure.

FIG. 19 illustrates a modified expandable retrieval device 100 having several features in common with the retrieval devices 100 illustrated in FIGS. 1-18. Accordingly, common features are designated with the same numbering as used in FIGS. 1-18, and the description above will be understood to apply to the retrieval device 100 of FIG. 19.

As shown in FIG. 19, the end frame segments 110a, the middle frame segment 110b, and/or transitions (e.g., tapered portions) there between and/or formed thereby can provides one or more features for interacting with a thrombus. For example, the end frame segments 110a, the middle frame segment 110b, and/or a transition (e.g., tapered portions) there between can define a blade feature 132 that faces axially toward the middle frame segment 110b and/or a proximal end of the retrieval device 100. The blade feature 132 can be configured to cut, engage, or otherwise interact with a thrombus upon contact therewith.

While the retrieval devices described herein have the features shown, it will be understood that a variety of different retrieval devices and other devices can be used with the delivery systems described herein. Various features are set forth below by way of example, and not by limitation.

Regarding such retrieval devices and other devices, the material(s) for forming the frame 110, struts 112, and/or protruding features 120 described herein can be selected based on mechanical and/or thermal properties, such as strength, ductility, hardness, elasticity, flexibility, flexural modulus, flexural strength, plasticity, stiffness, emissivity, thermal conductivity, specific heat, thermal diffusivity, thermal expansion, any of a variety of other properties, or a combination thereof. If formed from a material having thermal properties, the material can be activated to deliver thermal treatment to the desired treatment site. Regardless of the material, the frame 110, struts 112, and/or protruding features 120 can be formed from a tube or a wire, such as a solid wire, by laser cutting or other suitable techniques. When formed from the wire, a portion of the wire can be removed by chemical etching or another suitable method to create an inner dimension of the retrieval device.

The retrieval device 100 can be sized and shaped for positioning within various body lumens, including blood vessels, while not rupturing the vessel. For example, several retrieval devices and other structures can have radial strength without causing dissection or damage thereto. Vessels in which the retrieval devices described herein may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. The retrieval device 100 can have a variety of shapes, including a cube, a rectangular prism, a cylinder, a cone, a pyramid, or variations thereof.

The retrieval device 100 having protruding features 120 can include a variety of dimensions (in both the low-profile delivery state and expanded deployed state). These embodiments can provide for expansion that enables usage in a variety of situations covering a wide range of dimensions, such as to treat and/or prevent dissection. Regardless of the shape, retrieval devices can have a length of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 30 mm, about 40 mm, about 50 mm, about 60 mm, about 70 mm, about 80 mm, about 90 mm, or about 100 mm. In addition, a retrieval device shaped into a cube, a rectangular prism, or a pyramid can have a width of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, or about 30 mm. Moreover, a retrieval device shaped into a cylinder or a cone can have a diameter of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, about 30 mm, about 35 mm, about 40 mm, or about 50 mm. The width or the diameter of the retrieval device 100 can decrementally decrease along a length of the retrieval device 100. In addition, the retrieval device 100 can be sized and shaped to prepare the body lumen for certain procedures, such as a retrieval device positioning procedure.

The retrieval device 100 and/or other expandable structures in the expanded state can have a cross-sectional dimension of about 2 mm to about 10 mm. For example, the frame 110 can have a cross-sectional dimension of about 1 mm to about 9 mm and the protruding features 120 can each have a length from about 0.1 mm to about 4.5 mm. In some embodiments, the retrieval device 100 has an overall cross-sectional dimension of about 4 mm with the frame 110 having a cross-sectional dimension of about 2 mm and the protruding features 120 each having a length of about 1 mm. In some embodiments, the retrieval device 100 has an overall cross-sectional dimension of about 6 mm with the frame 110 having a cross-sectional dimension of about 4 mm and the protruding features 120 each having a length of about 1.5 mm. In further embodiments, the protruding features 120 can have a plurality of lengths such that the length of the protruding features 120 of a retrieval device or other expandable structure differs. For example, a retrieval device can include protruding features 120 having a length of about 0.2 mm, about 0.5 mm, and about 1 mm.

Profiles of the retrieval device 100 can be sized such that the retrieval device 100 are compatible with a wide range of catheter sizes. Embodiments in accordance with the present technology can include retrieval devices or other structures designed to receive a guidewire, such as guidewires having a diameter of 0.010, 0.014, 0.018, 0.035, or 0.038 inch. In several embodiments, the retrieval device 100 can be sized and designed for delivery via a micro-catheter that it is pushed through. In some embodiments, the retrieval device 100 can be incorporated into a delivery system, including modular or single unit delivery systems.

The retrieval device 100 can include a marking for visualization of the retrieval device 100 within the body lumen, such as one or more radiopaque markers. The radiopaque markers can be formed from Clearfil Photo Core PLT®, tantalum, titanium, tungsten, barium sulfate, and zirconium oxide, or another suitable radiopaque marking. The markings can be formed on a proximal portion of the retrieval device 100, a distal portion, an intermediate portion, or a combination thereof. The markings can be a band, a coil, a clip, filled into one or more portions of a tube in the retrieval device 100, plated onto one or more portions of the retrieval device 100, or a combination thereof. Regardless of the type of marking, the marking can be coined, swaged, wrapped, or encased along, or onto any portion of the retrieval device 100.

The retrieval device 100 can be flexible enough to track through various anatomical features, including those having a curvature. The flexible properties of the retrieval device 100 can be provided by the material from they are formed. In addition, flexible properties can also be provided by fracturing one or more of the members engaging with and extending between two or more rows of struts 112. Additionally, the retrieval device 100 can be readily deployed and expanded, and retracted and contracted. The retrieval device 100 can also be readily repositioned within a vessel or other body lumen.

In some embodiments, a drug-eluting compound is coated onto at least a portion of the protruding features 120, the frame 110, and/or the struts 112. The coating can be any suitable coating known to one of ordinary skill in the art suitable to deliver the drug. For example, suitable coatings include, but are not limited to a snow coating or a crystalline coating having edges configured to remain in the wall. The drug-eluting compound can be a synthetic or biological polymer coated into a variety of different patterns and thicknesses suitable for delivering the drug contained therein. In some embodiments, the protruding features 120 themselves may be composed of drug-eluting materials. The drug carried by the drug-eluting compound and/or the protruding features 120 in accordance with the present technology can be any drug suitable for treating the treatment site in which the retrieval device 100 will be placed and may or may not include an excipient. For example, the drug can be an anti-proliferative, an anti-neoplastic, a migration inhibitor, an enhanced healing factor, an immunosuppressive, an anti-thrombotic, a blood thinner, or a radioactive compound. In some embodiments, the drug-eluting compound and/or the protruding features 120 can carry more than one drug.

In some embodiments, the protruding features 120 can include textured (e.g., ribbed) surfaces which is expected to provide greater surface area for drug-delivery. Moreover, any protruding features 120 can include a textured surface such as a ribbed surface (vertical, horizontal, radial, or circular relative to a longitudinal plane of the protruding feature), a cross-hatched surface, an isotropic surface, or other surface types suitable for providing greater surface area for thrombus engagement.

The protruding features 120 can be sized and shaped to engage with and/or penetrate a thrombus, embolus, clot, occlusion, or a combination thereof. In addition, the retrieval device 100 can allow for blood to flow even while in the expanded position.

Further, it will be appreciated that retrieval device 100 can carry one or more protruding features 120 on one or more portions of the retrieval device 100. For example, the retrieval device 100 can carry about 5 protruding features, about 10 protruding features, about 15 protruding features, about 20 protruding features, about 30 protruding features, about 40 protruding features, about 50 protruding features, about 60 protruding features, about 70 protruding features, about 80 protruding features, about 90 protruding features, or about 100 protruding features. The protruding features 120 can be carried by the frame 110, the struts 112, or a combination thereof. The number of protruding features 120 can vary depending upon, for example, the target treatment site, the object being treated (e.g., thrombus), and/or the size of the retrieval device 100, etc. In addition, the protruding features 120 carried by the retrieval device 100 can be different types of the protruding features 120 disclosed herein.

The embodiments described herein provide delivery systems for one or more structures having a means for delivering drugs to a specific region within a body lumen, such as the vasculature, while still allowing fluid (e.g., blood) to flow through the treatment area where the structure has been placed and/or other devices or treatment means within the adjacent body lumen. In some embodiments, the fluid is temporary prevented from flowing through the treatment area while one or more regions of systems is delivered, deployed, positioned, and/or removed from the body lumen. In addition, the delivery systems can be configured to prepare the body lumen for treatment, by raking the retrieval device, pulling the retrieval device, turning the retrieval device, or a combination thereof, proximal or distal to the treatment site. In some embodiments, the delivery systems can be configured to rotate the retrieval device when mechanical force is applied.

Referring now to FIGS. 20-27, methods described herein provide delivery of the retrieval device 100 to a target delivery location by operation of a delivery device 90. While methods in their various stages are discussed and illustrated herein, it will be understood that multiple variations of each method are also contemplated. For example, the methods can be performed in various orders of operations, with additional operations, or with fewer operations.

Figure 20:
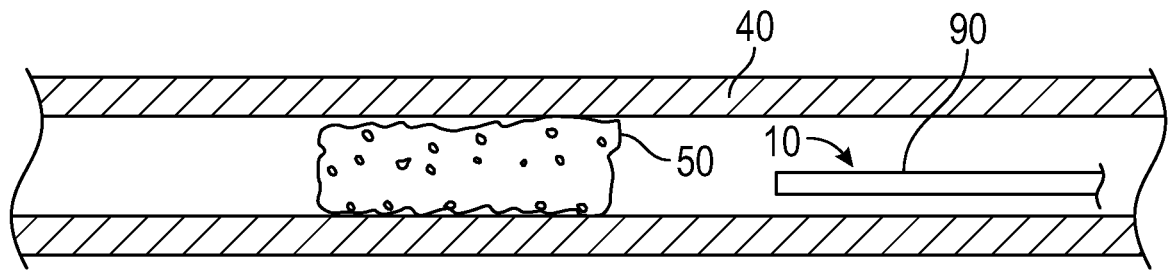
FIG. 20 shows a first stage of an example of a method for removing a thrombus from a patient, according to some embodiments of the present disclosure.

FIGS. 20-23 illustrate stages of an example of a method for thrombectomy. As shown in FIG. 20, a delivery device 90 of a delivery system 10 can be brought to a location within a blood vessel 40 containing a thrombus 50 or other mass. The delivery device 90 can be positioned upstream or downstream from the thrombus 50. The delivery device 90 can be positioned while a retrieval device is contained therein. Alternatively, the delivery device 90 can be positioned and the retrieval device can be advanced within the delivery device 90 at a later stage. The delivery device 90 can be positioned with the assistance of a guide wire and/or one or more other devices.

Figure 21:
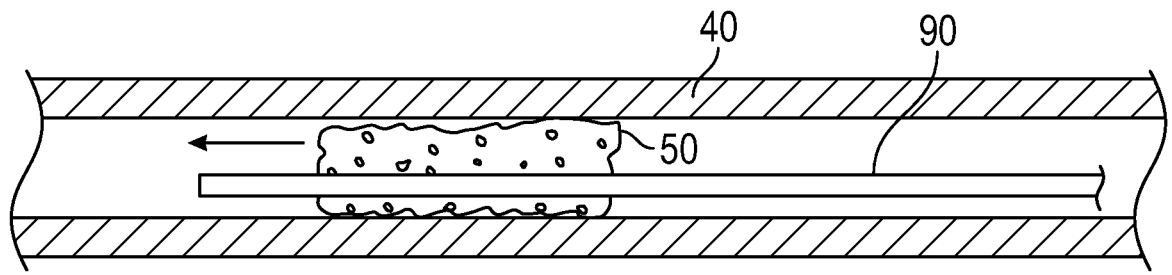
FIG. 21 shows a second stage of the method for removing the thrombus from the patient, according to some embodiments of the present disclosure.

As shown in FIG. 21, the delivery device 90 can be advanced within the blood vessel 40 and through the thrombus 50. Accordingly, a distal end of the delivery device 90 can be positioned distal to a distal end of the thrombus 50. Such operation can place the retrieval device in a position within the delivery device 90 such that the retrieval device spans at least a portion of the thrombus 50.

Figure 22:
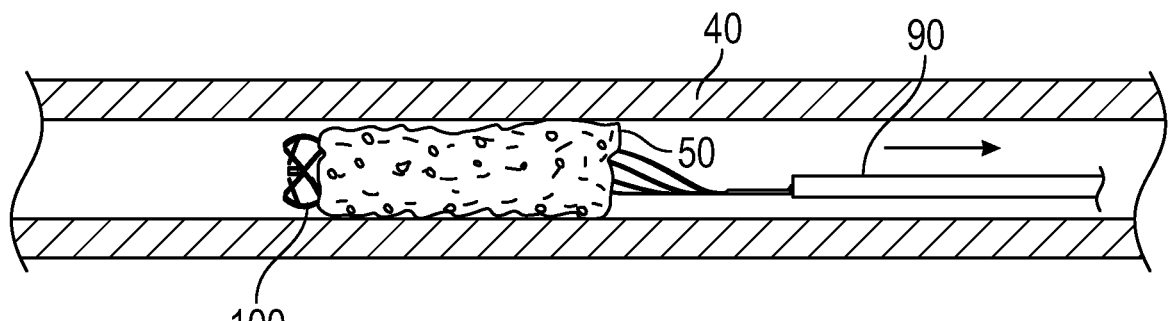
FIG. 22 shows a third stage of the method for removing the thrombus from the patient, according to some embodiments of the present disclosure.

As shown in FIG. 22, the delivery device 90 can be retracted proximally while the retrieval device 100 is maintained in a given position. As the delivery device 90 unsheathes the retrieval device 100, the retrieval device 100 can radially expand. The retrieval device 100 can self-expand upon release from a constraint. Additionally or alternatively, the retrieval device 100 can be expandable by an external stimulus (e.g., mechanical force, thermal stimulus, chemical reaction, etc.). For example, an expandable balloon device (not shown) can be provided to expand within the retrieval device 100. Such expansion can include expansion of the frame and/or the enlarged section. In the expanded configuration, the frame and/or the enlarged section can engage the inner walls of the blood vessel 40. Furthermore, expansion of the retrieval device 100 can include deployment of the protruding features 120 within the frame of the retrieval device 100 and into the thrombus 50. The retrieval device 100 can extend into and engage at least a portion of a length of the thrombus. As shown in FIG. 22, at least a portion of the retrieval device 100 can extend distal to and/or proximal to the thrombus 50. Where the retrieval device 100 includes a capture member 102, at least a portion of the capture member 102 can extend distal to at least a portion of the thrombus 50.

Figure 23:
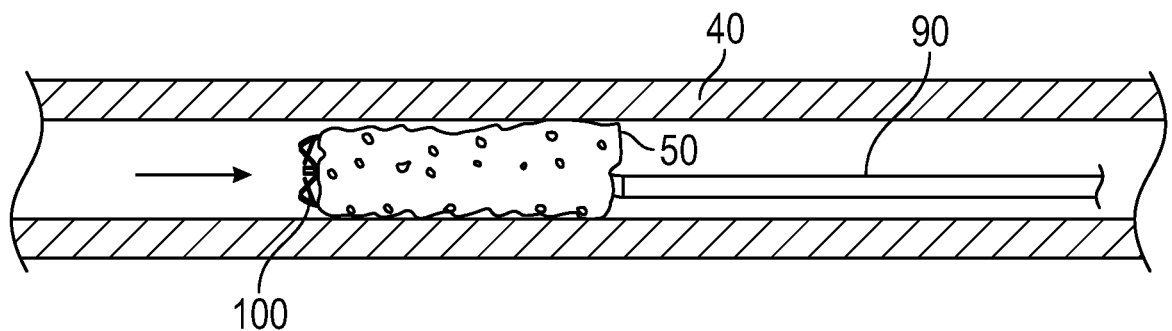
FIG. 23 shows a fourth stage of the method for removing the thrombus from the patient, according to some embodiments of the present disclosure.

As shown in FIG. 23, the retrieval device 100 can be retracted proximally toward and/or into the delivery device 90. Additionally or alternatively, the retrieval device 100 can be retracted proximally along with the delivery device 90 into another device. As the retrieval device 100 moves, the enlarged portion and/or the intermediate portion of the retrieval device 100 can separate the thrombus 50 from the walls of the blood vessel 40. Additionally, as the retrieval device 100 is retracted, the thrombus 50 can be carried by the retrieval device 100. For example, the protruding features 120 of the retrieval device 100 can engage the thrombus 50 at various portions thereof to urge the thrombus 50 proximally along with the retrieval device 100. The retrieval device 100 and the thrombus 50 can be moved until captured within the delivery device 90 and/or another device. Such capture can be facilitated and/or enhanced by aspiration of fluid into the distal end of the delivery device 90 and/or another device.

Figure 24:
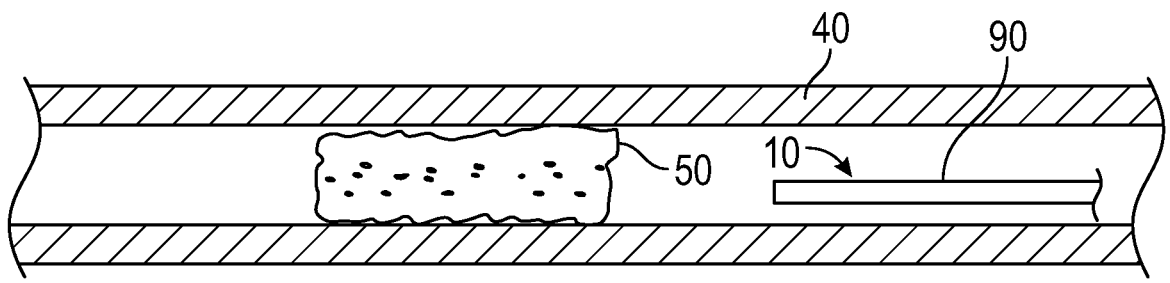
FIG. 24 shows a first stage of an example of a method for removing a thrombus from a patient, according to some embodiments of the present disclosure.

FIGS. 24-27 illustrate stages of another example of a method for thrombectomy. As shown in FIG. 24, a delivery device 90 of a delivery system 10 can be brought to a location within a blood vessel 40 containing a thrombus 50 or other mass. The delivery device 90 can be positioned upstream or downstream from the thrombus 50. The delivery device 90 can be positioned while a retrieval device is contained therein. Alternatively, the delivery device 90 can be positioned and the retrieval device can be advanced within the delivery device 90 at a later stage. The delivery device 90 can be positioned with the assistance of a guide wire and/or one or more other devices.

Figure 25:
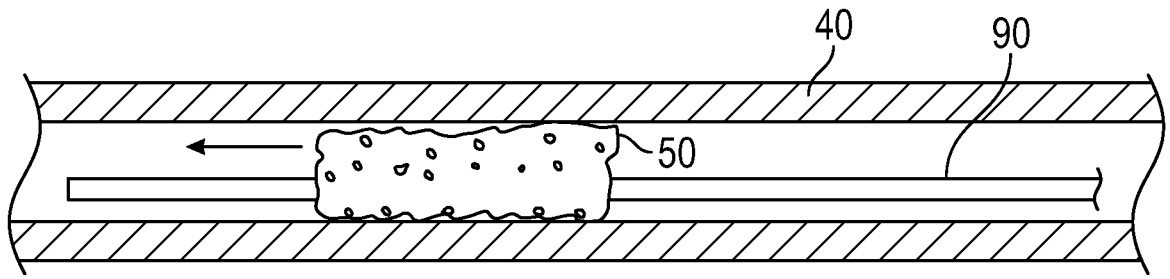
FIG. 25 shows a second stage of the method for removing the thrombus from the patient, according to some embodiments of the present disclosure.

As shown in FIG. 25, the delivery device 90 can be advanced within the blood vessel 40 and through the thrombus 50. Accordingly, a distal end of the delivery device 90 can be positioned distal to a distal end of the thrombus 50. Such operation can place the retrieval device in a position within the delivery device 90 such that the retrieval device is positioned at least partially or entirely distal to the thrombus 50.

Figure 26:
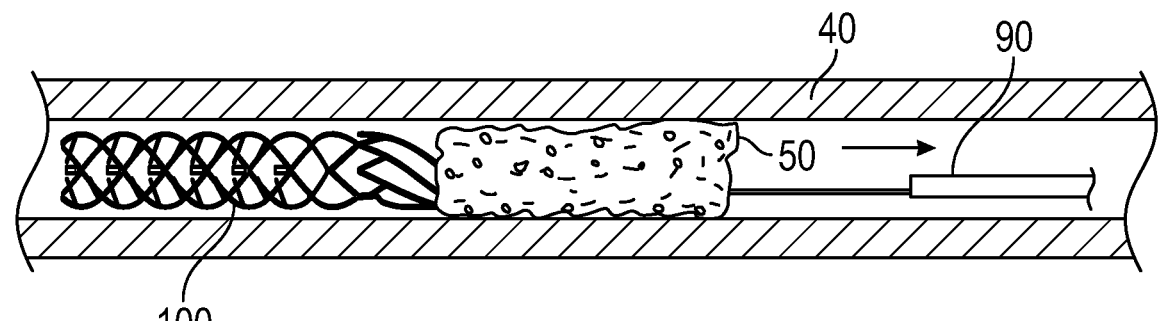
FIG. 26 shows a third stage of the method for removing the thrombus from the patient, according to some embodiments of the present disclosure.

As shown in FIG. 26, the delivery device 90 can be retracted proximally while the retrieval device 100 is maintained in a given position. As the delivery device 90 unsheathes the retrieval device 100, the retrieval device 100 can radially expand. The retrieval device 100 can self-expand upon release from a constraint. Additionally or alternatively, the retrieval device 100 can be expandable by an external stimulus (e.g., mechanical force, thermal stimulus, chemical reaction, etc.). For example, an expandable balloon device (not shown) can be provided to expand within the retrieval device 100. Such expansion can include expansion of the frame and/or the enlarged section. In the expanded configuration, the frame and/or the enlarged section can engage the inner walls of the blood vessel 40. Furthermore, expansion of the retrieval device 100 can include deployment of the protruding features 120 within the frame of the retrieval device 100. As shown in FIG. 26, at least a portion of the retrieval device 100 can be positioned at least partially or entirely distal to the thrombus 50. Where the retrieval device 100 includes a capture member 102, at least a portion of the capture member 102 can extend distal to at least a portion of the thrombus 50.

Figure 27:
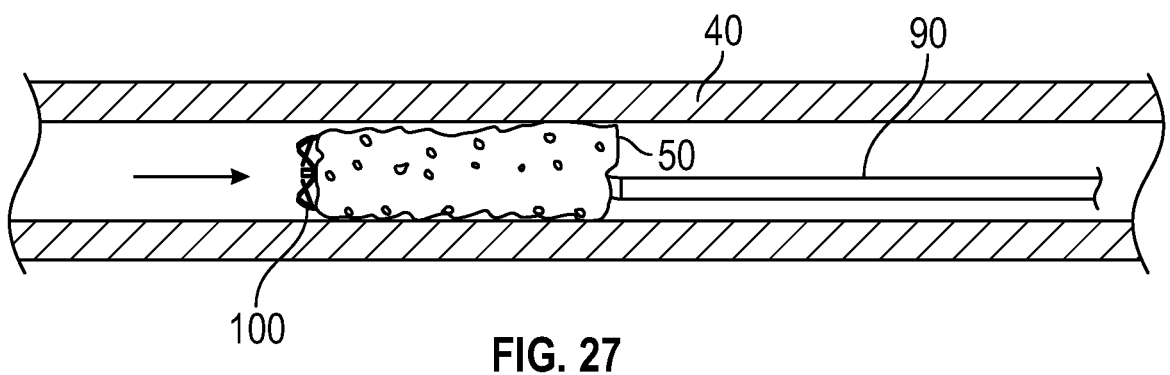
FIG. 27 shows a fourth stage of the method for removing the thrombus from the patient, according to some embodiments of the present disclosure.

As shown in FIG. 27, the retrieval device 100 can be retracted proximally toward and/or into the delivery device 90. As the retrieval device 100 was initially positioned and expanded at a location that is at least partially or entirely distal to the thrombus 50, the retrieval device 100 can be moved proximally into the thrombus 50 and thereby engage the thrombus 50. The retrieval device 100 can then engage at least a portion of a length of the thrombus 50. Additionally or alternatively, the retrieval device 100 can be retracted proximally along with the delivery device 90 into another device. As the retrieval device 100 moves, the enlarged portion and/or the intermediate portion of the retrieval device 100 can separate the thrombus 50 from the walls of the blood vessel 40. Additionally, as the retrieval device 100 is retracted, the thrombus 50 can be carried by the retrieval device 100. For example, the protruding features 120 of the retrieval device 100 can engage the thrombus 50 at various portions thereof to urge the thrombus 50 proximally along with the retrieval device 100. The retrieval device 100 and the thrombus 50 can be moved until captured within the delivery device 90 and/or another device. Such capture can be facilitated and/or enhanced by aspiration of fluid into the distal end of the delivery device 90 and/or another device.

Vessels in which the delivery systems, delivery devices, and/or retrieval devices described herein may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. Other vessels are likewise contemplated, and the delivery systems, delivery devices, and/or retrieval devices can be formed and/or selected according to a known destination and/or travel pathway within the body of a patient.

Various examples of aspects of the disclosure are described below as clauses for convenience. These are provided as examples, and do not limit the subject technology.

Clause A: a retrieval device comprising: a frame comprising interconnected struts and configured to expand from a collapsed configuration to an expanded configuration; protruding features extending radially inwardly from the frame when the frame is in the expanded configuration; and an anchor portion connected to a proximal end of the frame.

Clause B: a retrieval device comprising: a frame defining a lumen extending longitudinally through the frame and openings extending from an exterior of the frame to the lumen, the frame being configured to expand from a collapsed configuration to an expanded configuration; and protruding features extending from the frame, wherein: in the collapsed configuration, the protruding features extend longitudinally within the openings; and in the expanded configuration, the protruding features extend radially inwardly into the lumen.

Clause C: a method comprising: positioning at least a portion of a delivery system at least partially across a thrombus, the delivery system comprising a delivery device containing a retrieval device in a collapsed configuration while within a lumen of the delivery device; expanding the retrieval device outside of the delivery device; engaging the thrombus with the retrieval device while in an expanded configuration, wherein engaging the thrombus comprises contacting the thrombus with protruding features of the retrieval device, the protruding features extending radially inwardly from a frame of the retrieval device; retracting the retrieval device toward the delivery device.

One or more of the above clauses can include one or more of the features described below. It is noted that any of the following clauses may be combined in any combination with each other, and placed into a respective independent clause, e.g., clause A, B, or C.

Clause 1: the protruding features extend both radially inwardly and longitudinally away from the anchor portion.

Clause 2: the interconnected struts are arranged such that multiple ones of the interconnected struts are connected to each other to form a vertex, wherein one of the protruding features extends from the vertex.

Clause 3: the interconnected struts form a gap on a side of the vertex that is opposite the one of the protruding features.

Clause 4: each of the protruding features extends from the frame with a stem, the protruding features each terminating at an end thereof forming a head.

Clause 5: the head has a width that is greater than a width of the stem.

Clause 6: the head comprises multiple portions extending from the stem.

Clause 7: the head forms an opening.

Clause 8: the stem forms a patterned texture along a length thereof.

Clause 9: the protruding features are monolithically formed with the frame.

Clause 10: a capture member at a distal end of the frame, the capture member tapering from a cross-sectional dimension of the frame toward a central axis of the frame as the capture member extends distally away from the frame.

Clause 11: an anchor portion connected to a proximal end of the frame, the anchor portion being radially offset from a central axis of the frame; and an intermediate portion connecting the anchor portion to the frame, the intermediate portion forming a portion of the lumen.

Clause 12: the frame defines: a proximal frame segment; a middle frame segment; and a distal frame segment, wherein the proximal frame segment and the distal frame segment have cross-sectional dimensions that is larger than a cross-sectional dimension of the middle frame segment Clause 13: the protruding features comprise: proximal protruding features extending radially inwardly from the proximal frame segment; and distal protruding features extending radially inwardly from the distal frame segment; and the retrieval device further comprises middle protruding features extending radially outwardly from the middle frame segment.

Clause 14: expanding the retrieval device comprises expanding the frame into the thrombus.

Clause 15: expanding the retrieval device comprises transitioning the protruding features from positions within openings of the frame to positions within a lumen extending through the frame.

Clause 16: expanding the retrieval device comprises transitioning the protruding features from extending longitudinally to extending radially inwardly.

Accordingly, the present disclosure provides retrieval devices having inwardly facing protruding features that facilitate engagement and capture of a thrombus or other mass from a body lumen of a patient. The protruding features can deploy from a frame of the retrieval device to extend radially inwardly toward an opposing side of the frame. When deployed into a thrombus, the protruding features engage and urge the thrombus as the retrieval device moves to facilitate capture.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A retrieval device comprising:
   a frame comprising struts and configured to expand from a collapsed configuration to an expanded configuration, wherein the struts are connected to each other to form vertices;
   protruding features each extending from a corresponding one of the vertices and radially inwardly from the frame when the frame is in the expanded configuration, wherein the struts form gaps that allow the struts to move toward and away from each other to facilitate transition between the collapsed configuration and the expanded configuration, each of the gaps being on a side of the corresponding one of the vertices that is opposite a corresponding one of the protruding features, each of the gaps being defined by parallel edges of the struts on opposing sides of a corresponding one of the gaps; and
   an anchor portion connected to a proximal end of the frame.

2. The retrieval device of claim 1, wherein the protruding features extend both radially inwardly and longitudinally away from the anchor portion.

3. The retrieval device of claim 1, wherein each of the protruding features extends from the frame with a stem, the protruding features each terminating at an end thereof forming a head.

4. The retrieval device of claim 3, wherein the head has a width that is greater than a width of the stem.

5. The retrieval device of claim 3, wherein the head comprises multiple portions extending from the stem.

6. The retrieval device of claim 3, wherein the head forms an opening.

7. The retrieval device of claim 3, wherein the stem forms a patterned texture along a length thereof.

8. The retrieval device of claim 1, wherein the protruding features are monolithically formed with the frame.

9. The retrieval device of claim 1, further comprising a capture member comprising capture member struts extending from a distal end of the frame, the capture member tapering from a cross-sectional dimension of the frame toward a central axis of the frame as the capture member extends distally away from the distal end of the frame.

10. A retrieval device comprising:
    a frame comprising interconnected struts forming vertices and defining a lumen extending longitudinally through the frame and openings extending from an exterior of the frame to the lumen, the interconnected struts having portions that form parallel edges to define a gap on a proximal side of a corresponding one of the vertices and to allow the interconnected struts to move toward and away from each other to facilitate transition of the frame between a collapsed configuration and an expanded configuration; and
    protruding features each extending from the frame on a distal side of the corresponding one of the vertices, wherein:

in the collapsed configuration, the protruding features extend longitudinally within the openings; and in the expanded configuration, the protruding features extend radially inwardly into the lumen.

11. The retrieval device of claim 10, further comprising a capture member at a distal end of the frame, the capture member tapering from a cross-sectional dimension of the frame toward a central axis of the frame as the capture member extends distally away from the frame.

12. The retrieval device of claim 10, further comprising:

an anchor portion connected to a proximal end of the frame, the anchor portion being radially offset from a central axis of the frame; and an intermediate portion connecting the anchor portion to the frame, the intermediate portion forming a portion of the lumen.

13. The retrieval device of claim 10, wherein the frame defines: a proximal frame segment; a middle frame segment; and a distal frame segment, wherein the proximal frame segment and the distal frame segment have cross-sectional dimensions that are larger than a cross-sectional dimension of the middle frame segment.

14. The retrieval device of claim 13, wherein:

the protruding features comprise:

proximal protruding features extending radially inwardly from the proximal frame segment; and distal protruding features extending radially inwardly from the distal frame segment; and the retrieval device further comprises middle protruding features extending radially outwardly from the middle frame segment.

15. The retrieval device of claim 10, wherein the protruding features are monolithically formed with the frame.

16. A method comprising:

positioning at least a portion of a delivery system at least partially across a thrombus, the delivery system comprising a delivery device containing a retrieval device in a collapsed configuration while within a delivery device lumen of the delivery device the retrieval device comprising:

a frame comprising interconnected struts forming vertices and defining a retrieval device lumen extending longitudinally through the frame and openings extending from an exterior of the frame to the lumen, the interconnected struts having portions that form parallel edges to define a gap on a proximal side of a corresponding one of the vertices and to allow the interconnected struts to move toward and away from each other to facilitate transition of the frame between the collapsed configuration and an expanded configuration; and protruding features each extending from the frame on a distal side of the corresponding one of the vertices;

expanding the retrieval device outside of the delivery device;

engaging the thrombus with the retrieval device while in the expanded configuration, wherein engaging the thrombus comprises contacting the thrombus with the protruding features of the retrieval device, the protruding features extending radially inwardly from the frame; and retracting the retrieval device toward the delivery device.

17. The method of claim 16, wherein expanding the retrieval device comprises expanding the frame into the thrombus.

18. The method of claim 16, wherein expanding the retrieval device comprises transitioning the protruding features from positions within openings of the frame to positions within the retrieval device lumen extending through the frame.

19. The method of claim 16, wherein expanding the retrieval device comprises transitioning the protruding features from extending longitudinally to extending radially inwardly.

\* \* \* \* \*

UNITED STATES PATENT AND TRADEMARK OFFICE
CERTIFICATE OF CORRECTION

| | |
|---|---|
| PATENT NO. | : 11,877,762 B2 |
| APPLICATION NO. | : 17/085739 |
| DATED | : January 23, 2024 |
| INVENTOR(S) | : John Fulkerson et al. |

It is certified that error appears in the above-identified patent and that said Letters Patent is hereby corrected as shown below:

In the Claims

Column 20; Line 2 (Claim 16): "delivery device the" should read --delivery device, the--.

Signed and Sealed this
Thirtieth Day of April, 2024

Katherine Kelly Vidal
*Director of the United States Patent and Trademark Office*